(12) United States Patent
Cardoso Pacheco et al.

(10) Patent No.: US 12,226,196 B2
(45) Date of Patent: Feb. 18, 2025

(54) METHOD AND WEARABLE ELECTRONIC SYSTEM FOR PREDICTING THE HEART RATE OF A USER DURING A PHYSICAL ACTIVITY, AND, NON-TRANSITORY COMPUTER READABLE STORAGE MEDIUM

(71) Applicant: SAMSUNG ELETRÔNICA DA AMAZÔNIA LTDA., São Paulo (BR)

(72) Inventors: Andre Georghton Cardoso Pacheco, Campinas (BR); Frank Alexis Canahuire Cabello, Campinas (BR); Otavio Augusto Bizetto Penatti, Campinas (BR); Sunmin Lee, Suwon-si (KR); Hyunsu Kim, Suwon-si (KR); Donghyun Lee, Suwon-si (KR)

(73) Assignee: SAMSUNG ELETRONICA DA AMAZONIA LTDA., Campinas (BR)

( * ) Notice: Subject to any disclaimer, the term of this patent is extended or adjusted under 35 U.S.C. 154(b) by 375 days.

(21) Appl. No.: 17/679,815

(22) Filed: Feb. 24, 2022

(65) Prior Publication Data
US 2023/0190120 A1    Jun. 22, 2023

(30) Foreign Application Priority Data
Dec. 17, 2021 (BR) ...................... 10 2021 025682-6

(51) Int. Cl.
*A61B 5/024* (2006.01)
*A61B 5/00* (2006.01)
*A61B 5/11* (2006.01)

(52) U.S. Cl.
CPC ...... *A61B 5/02416* (2013.01); *A61B 5/02438* (2013.01); *A61B 5/1118* (2013.01);
(Continued)

(58) Field of Classification Search
None
See application file for complete search history.

(56) References Cited

U.S. PATENT DOCUMENTS 10,398,383 B2   9/2019  van Dinther et al.
10,405,760 B2   9/2019  Presura et al.
(Continued)

FOREIGN PATENT DOCUMENTS

EP       2992817 A1     9/2016
WO    WO2013038296 A1  3/2013

OTHER PUBLICATIONS

"Trapezoidal Rule" Aug. 4, 2020, Wikipedia. Retrieved from: https://web.archive.org/web/20200804073418/https://en.wikipedia.org/wiki/Trapezoidal_rule (Year: 2020).*
(Continued)

*Primary Examiner* — Michael W Kahelin
*Assistant Examiner* — Luke M Stanley

(57) ABSTRACT

A method for predicting heart rate (HR) of a user during a physical activity, comprising: monitoring the user during the physical activity with an wearable electronic device comprising a photoplethysmography (PPG) sensor, an accelerometer, a memory and a processor; wherein the memory is configured to store user demographic data, PPG data and accelerometer data detected by the PPG sensor and the accelerometer, respectively. The method includes computing a PPG heart rate estimation and a PPG quality flag using the PPG data and accelerometer data, wherein the PPG quality flag indicates whether the PPG data is reliable or not; computing an exponential heart rate estimation by applying the PPG heart rate estimation, the PPG quality flag and the user's demographic data on an exponential approximation
(Continued)

model; if the PPG quality flag is reliable, outputting the PPG heart rate estimation; otherwise, outputting the exponential heart rate estimation.

17 Claims, 5 Drawing Sheets

(52) U.S. Cl.
CPC ............ *A61B 5/681* (2013.01); *A61B 5/7203* (2013.01); *A61B 5/7221* (2013.01); *A61B 2562/0219* (2013.01)

(56) References Cited

U.S. PATENT DOCUMENTS

| | | | |
|---|---|---|---|
| 10,426,359 B2 | 10/2019 | Gopalakrishnan et al. | |
| 10,874,345 B2 | 12/2020 | Gowda et al. | |
| 10,893,815 B2 | 1/2021 | Pande et al. | |
| 2007/0250121 A1* | 10/2007 | Miesel | A61N 1/3615 607/3 |
| 2014/0213858 A1* | 7/2014 | Presura | A61B 5/0205 600/301 |
| 2015/0150491 A1* | 6/2015 | Yamato | A61B 5/1123 702/141 |
| 2015/0173627 A1* | 6/2015 | Fujii | A61B 5/681 600/483 |
| 2016/0058367 A1* | 3/2016 | Raghuram | A61B 5/681 600/479 |
| 2017/0127960 A1 | 5/2017 | Jang et al. | |
| 2017/0238875 A1* | 8/2017 | Olivier | A61B 5/02438 |
| 2017/0251935 A1 | 9/2017 | Yuen | |
| 2019/0090756 A1* | 3/2019 | Lu | A61B 5/7275 |
| 2020/0196897 A1* | 6/2020 | Biswas | A61B 5/02416 |
| 2022/0151512 A1* | 5/2022 | Sergeev | A61B 5/026 |

OTHER PUBLICATIONS

A.V. J. Challoner et al., "A Photoelectric Plethysmograph for the Measurement of Cutaneous Blood Flow", Phys. Med. Biol., vol. 19, No. 3, 317-328, 1974.
Maria S. Zakynthinaki, "Modelling Heart Rate Kinetics" PLOS ONE DOI: 10.1371/journal.pone.0118263, Apr. 13, 2015.
A.V. Hill et al., "Muscular Exercise, Lactic Acid, and the Supply and Utilisation of Oxygen—Parts I-III.", https://royalsocietypublishing.org, downloaded Feb. 22, 2022.
Ryan McConville et al., "Online Heart Rate Prediction using Acceleration from a Wrist Worn Wearable", arXiv: 1807.04667v1 [stat.AP], Jun. 25, 2018.
Jae Wook Shin et al., "Noise-Robust Heart Rate Estimation Algorithm from Photoplethysmography Signal with Low Computational Complexity" Department of Medical and Mechatronics Engineering, Soonchunhyang University, Asan, Republic of Korea; Hindawi; Journal of Healthcare Engineering; vol. 2019, Article ID 6283279, 7 pages.
Zhilin Zhang et al., "TROIKA: A General Framework for Heart Rate Monitoring Using Wrist-Type Photoplethysmographic Signals During Intensive Physical Exercise" IEEE Transactions on Biomedical Engineering, vol. 62, No. 2, Feb. 2015; 10 pages.

* cited by examiner

METHOD AND WEARABLE ELECTRONIC SYSTEM FOR PREDICTING THE HEART RATE OF A USER DURING A PHYSICAL ACTIVITY, AND, NON-TRANSITORY COMPUTER READABLE STORAGE MEDIUM

CROSS-REFERENCE TO RELATED APPLICATION(S)

This application is based on and claims priority under 35 U.S.C. § 119 to Brazilian Patent Application No. BR 10 2021 025682-6, filed on Dec. 17, 2021, in the Brazilian Intellectual Property Office, the disclosure of which is incorporated by reference herein in its entirety.

FIELD OF THE DISCLOSURE

The presented invention describes a method for estimating the heart rate (HR) of a person using a wearable electronic system (e.g., smartwatch) during physical exercises. More specifically, the invention refers to a Personalized Exponential Model (PEM) and takes as input only a 3-axis accelerometer signal, the user's demographics (i.e., age, height, weight, and gender), and an initial estimation of the HR.

DESCRIPTION OF RELATED ART

Over the past few years, the number of wearable devices, in particular smartwatches, has substantially increased worldwide and it is expected to reach approximately one billion devices by 2022. An important feature that strongly contributed to the success of such devices is the possibility to get prompt insights about the health and well-being of a user in a fast and non-invasive way. These insights are obtained by processing different pieces of information that are provided by the device such as sleep time, step count, activity pattern, and heart rate (HR), which is probably the most important measurement delivered by the device.

Real-time HR estimation in wearable devices mostly relies on photoplethysmography (PPG), which is a non-invasive and low-cost optical technique that may be applied to measure changes in blood volume using LEDs and photodiodes.

The photoplethysmography (PPG) is classical optical technique that may be applied to detect changes in the blood flow, consequently, to measure the HR, that was first disclosed in "*A photoelectric plethysmograph for the measurement of cutaneous blood flow*" (10.1088/0031-9155/19/3/003). Since it was a straightforward and non-invasive way to estimate HR and has multiple clinical applications, this technique has been embedded into different medical devices such as pulse oximeters and blood pressure measurement systems. Over the past few years, the PPG has become a key technique that has been contributing to the success of the wearable devices, in particular, smartwatches.

Several apparatuses and/or mechanisms have been proposed to embed PPG sensors in wearable devices to estimate the user's vital signals, such as heart rate. To name a few, in "Automated detection of breathing disturbances" (U.S. Ser. No. 10/874,345B2) it was proposed a method to obtain a sleep fitness and breathing disturbance score based on PPG signals; in "Blood pressure sensors" (US20170251935A1) is presented an algorithm to measure the blood pressure using the PPG sensor data representing blood volume pulses of variable amplitude. Lastly, in "Methods and systems for arrhythmia tracking and scoring" (U.S. Ser. No. 10/426,359B2) machine learning methods use the PPG signals to detect the presence of significant arrhythmias in the user's heart.

Although this technique has become the standard approach to estimate HR in these devices, the PPG signal is vulnerable to motion artifacts (MA), which is a type of noise derived from user movements. As a consequence, the HR estimated from PPG signals is strongly affected during physical exercises, in particular, in wrist-based devices, such as smartwatches, since they are more susceptible to movements than a device attached in the chest, for example. Therefore, mitigating MA is one of the major challenges in PPG-based heart rate monitoring. In addition, methods addressed to handle such a problem must conciliate the estimation accuracy with memory and computational constraints inherent to the device characteristics.

A typical approach to deal with MA observed from prior art is to preprocess the PPG signal in order to remove the presence of MA before estimating the HR. Some methods aim to remove the MA without using any other signal information. However, in most of the methods, accelerometer signals are used to get an insight about the motion information in order to remove it from the PPG signal. Such approaches have demonstrated to be useful when the device is exposed to light movements. Nonetheless, when the user performs an activity that demands strong movements (e.g., a running exercise session), these approaches are not enough to clean the MA from the PPG signal. As a consequence, the user's HR estimated during this situation may be far from the correct measurement. In order to avoid showing wrong measurements to the users, it is a common strategy to incorporate a PPG signal quality estimation algorithm into the HR estimation pipeline. This algorithm aims to generate a flag to indicate when the HR estimated from the signal is reliable or not. Usually, whenever the flag is unreliable, the device is configured to not show the HR on its screen. Obviously, it harms the user experience, which may lead to a negative view of the device.

Naturally, there are different methodologies to deal with it. For example, in "Electronic device and method for measuring vital signal" (EP2992817A1) the vital signal is measured only when the motion is less than or equal to a threshold. Obviously, such threshold aims to prevent wrong vital signals estimations caused by MA. However, this is a naive approach, and such devices may not work properly during physical exercises session, which is a quite important case of use of wearables in general.

Other approaches to reduce the impact of MA in the PPG signal is to preprocess it in order to identify the presence of MA on it. In "Heart rate measurement and a photoplethysmography (PPG) heart rate monitor" (U.S. Ser. No. 10/893,815B2) it is applied a Normalized Least Mean Squares (NLMS) adaptive filter to reduce the MA and a single Fourier Transform on the motion compensated PPG signal to generate a frequency domain PPG signal to estimate the HR based on it.

In "Motion artifact reduction using multi-channel PPG signals" (U.S. Ser. No. 10/398,383B2) the MA is identified and reduced by applying an Independent Component Analysis (ICA) on multiple PPG channels that identifies the noise space related to each independent component. In other methods, accelerometer signals are used to get an insight about the motion information in order to remove it from the PPG signal.

In "TROIKA: A General Framework for Heart Rate Monitoring Using Wrist-Type Photoplethysmographic Signals During Intensive Physical Exercise" (10.1109/TBME.2014.2359372) and in "Noise-robust heart rate estimation algorithm from photoplethysmography signal with low computational complexity" (10.1155/2019/6283279) it is applied the Singular Spectrum Analysis (SSA) decomposition of the PPG signal and the accelerometer signal to perform MA cancellation. Despite achieving fair results for light exercises, the method struggles to keep the same performance for exercises with strong movements (e.g. a running session), in particular for wrist-type devices.

The main goal of the approaches previously described is basically to clean the PPG signal in order to improve the vital signals estimations.

A different perspective is to use methods to support the PPG based estimation that do not rely in the same signal. For example, in "Online Heart Rate Prediction using Acceleration from a Wrist Worn Wearable" (1807.04667) it is proposed a methodology based on Random Forest Regression and active learning to predict the HR using only an acceleration signal. However, the method is computational expensive in terms of memory, which makes it unfeasible to embed in low-resource devices such as wearables. In addition, it was not designed to work during physical exercises, and it was validated using only four subjects.

A simpler way to model the HR kinetics was proposed in "Muscular Exercise, Lactic Acid, and the Supply and Utilization of Oxygen" (10.1093/qjmed/os-16.62.135) in which points out that the cardiovascular response to a constant physical exercise may be approximated by an exponential function over time. In this sense, in "Device and method for estimating the heart rate during motion" (WO2013038296A1) it is proposed a method to estimate the HR based on an exponential function and a motion measurement.

The aforementioned apparatus and mechanisms assume a constant value for the HR according to a given motion information. From this value, an exponential interpolation is applied to replace possible wrong HR measurements caused by MA. As observed by the present inventors, such assumption is quite strong and may not be feasible in most of the occasions.

Other similar ideas are proposed in "Heart rate monitor systems" (U.S. Ser. No. 10/405,760) and "Method and apparatus for estimating heart rate based on movement information" (US2017127960A1). Both methods propose one or more regression models to estimate HR using the motion information obtained from physical activities. In U.S. Ser. No. 10/405,760, the HR estimation obtained from a single regression model is compared with the one obtained from a PPG-based method to identify possible artifacts in the signal. On the other hand, US2017127960A1 combines two different regression models to estimate the HR without using an optical sensor such as a PPG. The first one is based on the average of the HR and the moving information of multiple users and the second one uses previous data from the current user to fine-tune the prediction. It also combines the HR estimations obtained from PPG and non-PPG based methods to improve the final HR estimation. However, these methods rely on the comparisons between the HR estimation from motion information and a PPG-based method.

As it can be seen, different strategies were implemented to try to overturn the issues related to the MA in the HR predictions. However, the state of art lacks a solution capable of dynamically updating the HR according to the current value of the motion information obtained from an accelerometer signal. In addition, there is a need for a solution that can present a continual learning approach to personalize the estimator in real-time without the need to store data from past HR measurements.

SUMMARY OF THE INVENTION

Aiming at solving the aforementioned limitations and difficulties related to support the PPG-based HR prediction when the signal is affected by MA or any other type of noise, in particular, during walking and/or running sessions, the present invention proposes the Personalized Exponential Model (PEM), an approach that learns to estimate the HR in real-time during physical exercises using 3-axis of an accelerometer signal, the user's demographics, and an HR starting point. In addition, it uses a continual learning approach that allows personalization in real-time without the need of storing past predictions on memory. In this sense, our method is able to better map the user's heart rate kinetics, which results in a more reliable HR estimation.

In order to achieve this, the present invention proposes a method for predicting the heart rate (HR) of a user during a physical activity, the method comprising: monitoring the user during the physical activity with an wearable electronic device comprising a photoplethysmography (PPG) sensor, an accelerometer, a memory and a processor; wherein the memory is configured to store user demographic data, PPG data and accelerometer data detected by the PPG sensor and accelerometer, respectively; computing a PPG heart rate estimation and a PPG quality flag using the PPG data and accelerometer data, wherein the PPG quality flag indicates whether the PPG data is reliable or not; computing an exponential heart rate estimation by applying the PPG heart rate estimation, the PPG quality flag and the user's demographic data on an exponential approximation model; if the PPG quality flag is reliable, outputting the PPG heart rate estimation; otherwise, outputting the exponential heart rate estimation.

The present invention also related to a wearable electronic system and a non-transitory computer readable storage medium adapted for performing said proposed method for predicting the HR of a user during a physical activity.

BRIEF DESCRIPTION OF THE DRAWINGS

The invention is explained in greater detail in the following according to the figures.

DETAILED DESCRIPTION OF THE INVENTION

The present invention aims at providing a new method for predicting the HR of a user during a physical activity. For this, the present invention proposes the Personalized Exponential Model (PEM), an approach that learns to estimate the HR in real-time during physical exercises using 3-axis of an accelerometer signal, the user's demographics, and an HR starting point. In addition, it uses a continual learning approach that allows personalization in real-time without the need of storing past predictions on memory. In this sense, our method is able to better map the user's heart rate kinetics, which results in a more reliable HR estimation.

Figure 1A:
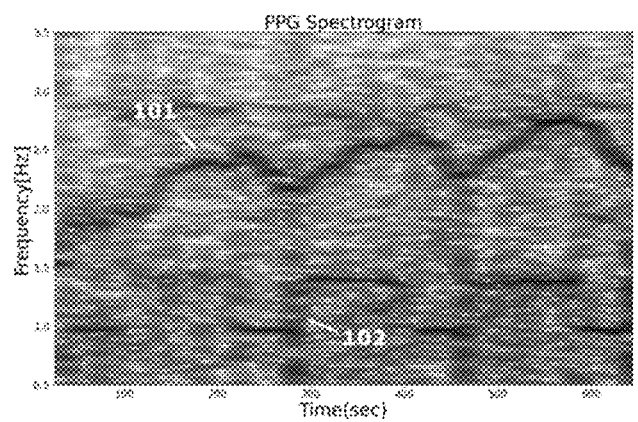
FIGS. 1A and 1B show two examples of spectrograms obtained from two different PPG signals collected during a running workout session, according to an embodiment of the present invention.
Figure 1B:
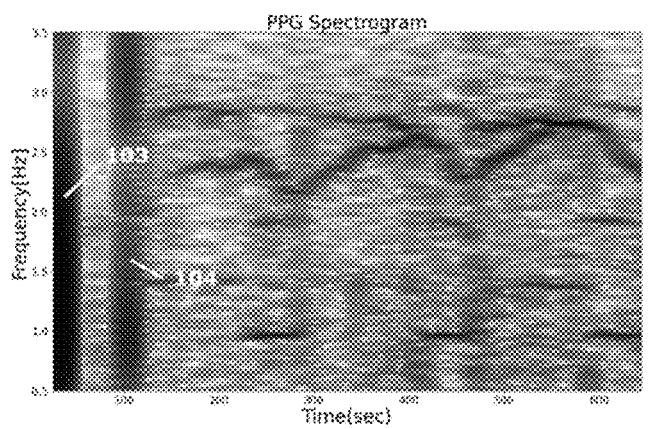

As previously discussed, estimating the heart rate (HR) from photoplethysmography (PPG) sensors embedded in wearable devices during physical exercises is a challenging task due to different issues. In addition, Motion Artifacts (MA) is the type of noise responsible for causing most of the wrong PPG-based HR estimations in wrist-type devices (e.g. smartwatches). Nonetheless, there are other problems such as sweating and loosely placed devices that also contribute to poor estimations and are quite hard to be detected by the current methods that deal with this issue. In order to illustrate how the noise affect the PPG signal, and consequently, the HR estimation, FIGS. 1A and 1B show two examples of spectrograms obtained from two different PPG signals collected during a running workout session.

In the first spectrogram (FIG. 1A), it is possible to distinguish the HR spectrum 101 from the MA 102. In the second one (FIG. 1B), it is possible to see strong disruptions 103 and 104 that are caused by MA and other types of noise. For this case, it is quite difficult to extract the spectrum for the HR curve.

Figure 2:
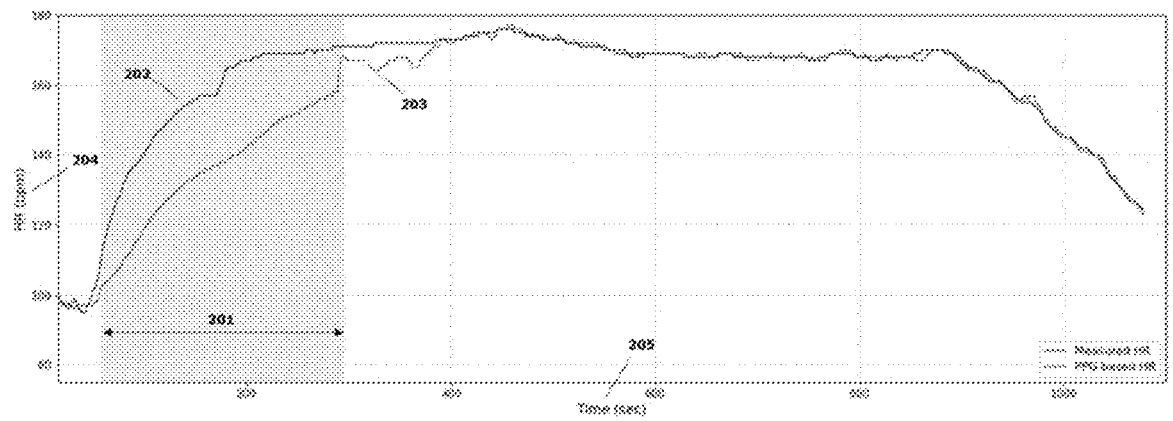
FIG. 2 shows an illustration of the poor HR estimation during a running workout session, according to an embodiment of the present invention.

In FIG. 2, it is illustrated an example of poor HR estimation caused by noise in the PPG signal also during a running workout session. The plot shows the HR estimation throughout the time where the Y-axis 204 and X-axis 205 represent the HR in beats per minute (bpm) and the time in seconds (sec), respectively. The signal 202 indicates the reference HR obtained from an electrocardiogram (ECG) heart rate sensor attached to the user's chest, while signal 203 indicates a PPG-based HR estimation obtained from a smartwatch using a common method for reducing the impact of the MA in the PPG signal. Lastly, the gray area 201 represents the period of time in which the PPG signal is strongly affected by noise and any estimation achieved using this part of the signal is indicates as unreliable.

In order to tackle this problem, the present invention proposes a method for HR estimation during strong movements without using the PPG signal, which would be unreliable. In this way, the proposed method is applied to support the PPG-based HR estimation by replacing the poor estimation achieved within the gray area 201 by one closer to the reference signal 202.

More specifically, the present invention proposes a method for predicting the heart rate (HR) of a user during a physical activity, the method comprising: monitoring the user during the physical activity with an wearable electronic device comprising a photoplethysmography (PPG) sensor, an accelerometer, a memory and a processor; wherein the memory is configured to store user demographic data, PPG data and accelerometer data detected by the PPG sensor and accelerometer, respectively; computing a PPG heart rate estimation and a PPG quality flag using the PPG data and accelerometer data, wherein the PPG quality flag indicates whether the PPG data is reliable or not; estimating an exponential heart rate estimation by applying the PPG heart rate estimation, the PPG quality flag and the user's demographic data on an exponential approximation model; if the PPG quality flag is reliable, outputting the PPG heart rate estimation; otherwise, outputting the exponential heart rate estimation.

Therefore, the present invention proposes a lightweight HR estimator method that, in real-time and in a recurrent way, estimates the next HR using as inputs 3-axis of an accelerometer signal, the user's demographics (age, gender, height, and weight), and the previous HR. The proposed estimator does not depend on the PPG signal to estimate the HR. However, it does not aim to replace PPG-based HR estimators, but to support them when the PPG signal is strongly affected by MA or any other type of noise, in particular, during physical exercises, which is when the majority of the wrong HR estimations occur.

Beyond the aforementioned input data, the proposed invention also receives, from the PPG-based approach, the HR estimated and the PPG signal quality information (hereinafter referred to as quality flag) that indicates if the signal is reliable or not. As such, we may see the proposed invention as another block that is attached to the PPG-based method output. According to the quality flag, it determines the value of the HR that is returned. In summary, if the quality flag is reliable, the PPG-based estimation will always be outputted. On the other hand, if it is unreliable, the HR estimation results from a composition obtained from both methods, preferably, with a smooth transition between them. In this sense, the present invention is preferably composed of a complete pipeline that includes:
- a preprocessing method to generate an activity level measurement;
- an Exponential Approximation (EA) model that estimates the HR;
- a continual learning approach to personalize the EA model in real-time without storing past predictions on the device's memory;
- a manager block that uses the quality flag to ensure a smooth transition between the exponential model and the PPG-based approach whenever the quality flag is unreliable.

This entire pipeline is named Personalized Exponential Model (PEM) and is designed to run in real-time in devices with strong memory restrictions, which is mandatory to allow its deployment in wearable devices.

More specifically, the first embodiment of the present method will be described with reference to FIG. 3, which shows an illustrative pipeline that represents the present method according to a preferred embodiment of the present invention.

In order carry out the proposed invention, it is necessary to monitor the user during the physical activity via a wearable electronic device comprising a photoplethysmography (PPG) sensor and an accelerometer. Furthermore, the wearable device also comprises a memory for storing the user's demographics 303, the PPG data 301 and accelerometer data 302 detected by the PPG sensor and accelerometer, respectively. Preferably, considering the memory limitations of wearable devices, the memory may store such data temporarily, being used for the calculation and being discarded or overwritten during future iterations of the method. However, the memory may alternatively be used for storing such data for longer periods, depending on the availability of memory in the electronic device.

In addition, the wearable electronic device may also comprise a processor for processing and executing the steps of the proposed method.

Figure 3:
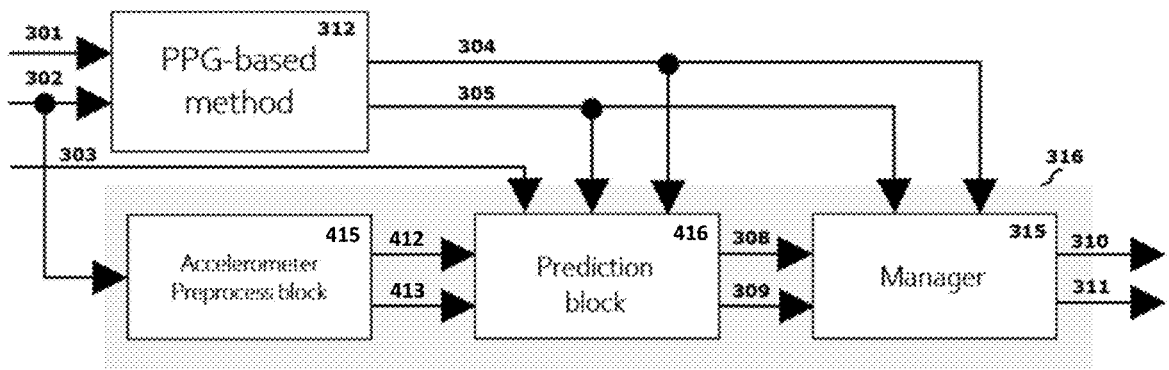
FIG. 3 shows an illustration of the complete pipeline of the proposed invention, according to an embodiment of the present invention.

In FIG. 3, 312 represents step of computing a PPG heart rate estimation 304 and a PPG quality flag 305 using the PPG data 301 and accelerometer data 302. The PPG quality flag 305 indicates whether the PPG data 301 is reliable or not. The PPG-based method refers to the prediction of the heart rate and the PPG quality flag 305 with basis on both the signals provided by the PPG sensor and the accelerometer. However, the motion artifacts affect the results. Accordingly, the present invention proposes the use of a secondary heart rate estimation method.

The proposed method is composed of three main blocks: (1) a accelerometer preprocess block 415, (2) a prediction block 416, and (3) a manager block 315. Particularly, the Personalized Exponential Model (PEM) is illustrated in pipeline 316 that shows all three blocks, how they communicate with each other, and how these blocks are integrated with a PPG based approach. The inputs are the PPG signal 301, 3-axis of an accelerometer signal 302, and the user's demographics 303 (age, weight, height, and gender). The outputs are the PPG-based HR estimation 304 and the quality flag 305.

The Accelerometer preprocessing block 415 receives the accelerometer signal 302 and returns a value that represents the level of movement 412 and another value that indicates the intensity of the physical activity 413. These values are sent to the prediction block 416 that also takes the user's demographics 303, PPG-based HR estimation 304, and quality flag 305 as input to produce the HR estimation based on the present model 308 and the personalization timer 309, which indicates for how long the predictor model was personalized using the user's data. The personalization algorithm, which is carried out in block 416, uses the user's data to update the model in order to improve its predictions. Finally, the manager block 315 gets as inputs the PPG-based HR estimation 304, quality flag 305, HR estimation based on the present model 308, and the personalization timer 309 to generate the final HR estimation 310 and the final quality flag 311. As previously mentioned, the exponential approximation block 316 is attached to the PPG-based approach and the manager block 315 ensures a smooth transition between the methods if the PPG signal is unreliable.

In view of the features above, the proposed invention presents the following main advantages.

It estimates the HR without using the PPG signal, which is the standard approach to obtain such measurement in wearable devices. As stated, this feature is important because it allows the method to cover poor estimations when the quality flag is unreliable. In other words, the accelerometer is not used to clean the PPG signal. Instead, the accelerometer is used as a main resource to predict the HR during a period of time in when the PPG is disturbed by noise.

It presents a strategy to personalize the prediction model in real-time using the own user's data. To do so, the present invention involves a learning approach to optimize the model whenever the PPG quality flag is reliable. Therefore, the model according to the present invention is capable of continuously learning, which is important to improve its predictions. It is important to note that the personalization algorithm does not hinder the model's performance in terms of computational time and memory burden, since it does not need to save past workout data.

The present method is agnostic to a PPG-based approach. In other words, the pipeline presented in FIG. 3 may be applied to improve any method in which the PPG signal is disrupted by noise.

Moreover, it demands less than 1 KB of memory for both HR estimation and personalization, which allows it to be easily embedded in wearable devices that have strong constraints in terms of memory.

Therefore, the present method can run completely on-device, which means that no cloud or local server is necessary for training the model. The model is constantly retrained on-device in real-time during physical activities, such, as a workout session. In addition, the on-device solution also has the advantage of keeping user's data privacy since no data needs to be shared or uploaded to a server neither for inference or training. All the steps of the method can be carried out on-device.

In the remaining of this section, the three main blocks depicted in FIG. 3 ill will be thoroughly described.

Accelerometer Preprocess and HR Prediction

Figure 4:
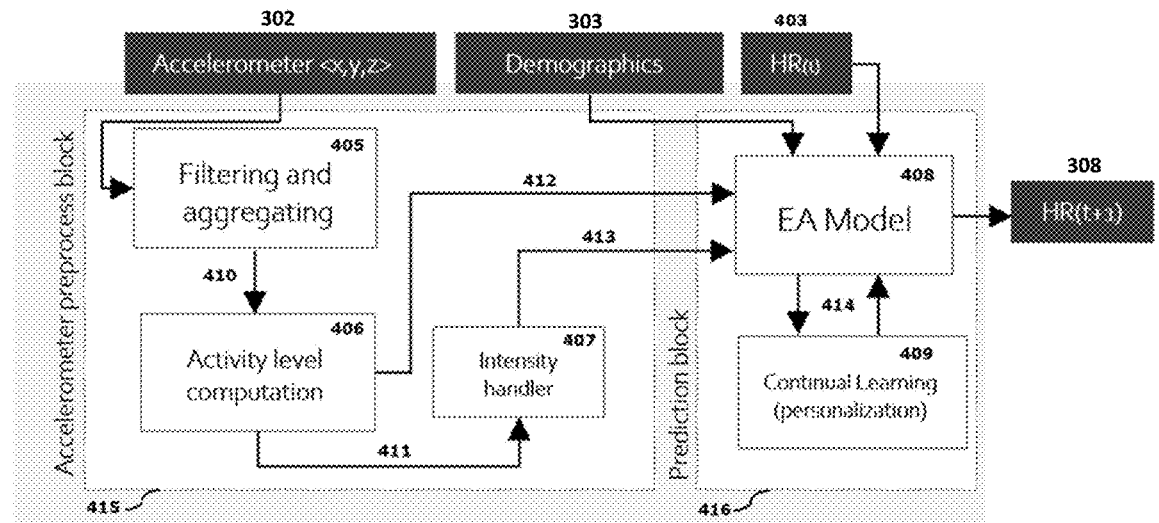
FIG. 4 shows a flowchart illustrating the accelerometer preprocess and prediction blocks of the proposed invention, according to an embodiment of the present invention.

In FIG. 4, the interactions between the accelerometer preprocess block 415 and the HR prediction block 416 are presented in detail. Each part of this figure is described in the following subsections.

Accelerometer Preprocess Block (415)

The accelerometer preprocess block 415 executes the step of determining the level of movement 412 and the intensity of the physical activity of the user 413 using the accelerometer data 302. Preferably, the accelerometer preprocess block 415 is designed to take 3-axis (x, y, z) of the accelerometer signal 302 in order to produce two values that represent the activity level (AL) 412 and intensity state of the workout 413. To do so, this block is composed of three different modules: filtering and aggregating 405, activity level computation 406, and intensity handler 407, which are thoroughly described as follows.

Filtering and Aggregating (405)

This module consists of two steps. First, the 3-axis of the accelerometer 302 are filtered using signal processing filters including, but not limited, a band-pass Finite Impulse Response (FIR) filter. This step aims to clean the accelerometer signal and reduce low frequency noise. Next, we aggregate the 3-axis of the accelerometer, which were filtered in the previous step, using a norm function such as:

$$agg(\alpha_x, \alpha_y, \alpha_z) = \alpha_x^2 + \sqrt{\alpha_y^2 + \alpha_z^2} \quad (1)$$

where $\alpha_x$, $\alpha_y$ and $\alpha_z$ represent the 3-axis coordinates of the accelerometer.

The aggregated accelerometer value 410 is used as input to the next module 406.

Activity Level Computation (406)

In this module, the aggregated signal 410 is integrated using a sliding window of time to obtain a raw value of the activity level $AL_{raw}$, which may be approximated, for example, by the trapezoidal rule:

$$AL_{raw} = \int_{t_1}^{t_2} agg(a) \approx \Delta a \sum_{k=1}^{N-1} agg(a_k) + \frac{agg(a_n) + agg(a_0)}{2} \quad (2)$$

where a=[$a_x$, $a_y$, $a_z$] and N is the number of data points within the window, which depends on the accelerometer signal frequency. The $AL_{raw}$ 411 is sent to the intensity handle module 407. The value indicated in 412 is the normalized version of the raw activity level. To achieve this value, we apply the clipping operation to ensure that 411 lies within [0, 1]. Next, we integrate it and normalize the result by dividing it by the size of the time window (i.e. $t_2-t_1$), which is the maximum value that the integral may assume.

Intensity Handler (407)

This module takes as input the raw activity level 411 in order to compute the intensity of the physical activity 413. This intensity may assume two states: low or high. To select this state, we define a threshold $\varphi_i$ that is obtained from data. If $\varphi_i < AL_{raw}$ for a predefined period of time, the state is low, otherwise, high. The selected state is used as input by the prediction block.

Prediction Block (416)

The prediction block 416 executes the step of estimating an exponential heart rate estimation 308 by applying the PPG heart rate estimation 304, the PPG quality flag 305 and the user's demographic data 303 on an exponential approximation model 408. It takes as inputs the user's demographics 303, which consists of age, weight, height, and gender, the HR estimation at time t 403, the activity level 412, and the intensity state 413 to estimate the HR at time t+1. The block is composed of two modules: the exponential approximation (EA) model 408 and the continual learning 409, which we detail in the following.

Exponential Approximation Model (408)

The exponential approximation (EA) model comes from the observation that the cardiovascular kinetics during physical exercised may be modeled by an exponential function over time [2, 3]. As such, we present a new dynamic and recursive model that is able to predict future HRs according to the following equation:

$$HR(t+1) = \tilde{HR} - [\tilde{HR} - HR(t)] \times e^{\frac{1}{\tau}} \quad (3)$$

wherein HR(t+1) is the predicted HR 404 and HR is defined as:

$$\tilde{HR} = D_s \times W^T + \{b_{low}, b_{high}\} \quad (4)$$

In this equation, $D_s$ is an array defined as [AL, BMI, age, male, female], where the AL is the activity level 412 and the remaining data are obtained from the demographics 303, i.e., BMI is the body mass index (weight/height$^2$) and the gender is mapped to male and female that may assume 1 or 0. In addition, the parameter b is determined according to the intensity of the physical activity 413.

As we may see, the exponential approximation model has only eight trainable parameters to predict the HR: W, $\tau$, $b_{low}$, and $b_{high}$. In summary, the predicted HR is obtained according to the previous HR and the $\tilde{HR}$, which is a measurement that indicates how much the predicted HR must increase or decrease from its previous value HR(t). This change is controlled by the exponential $$e^{-\frac{1}{\tau}}$$

that determines how fast or slow the HR(t+1) should increase or decrease. As previously stated, this is a recurrent model, i.e., we must know HR(t) in order to estimate HR(t+1) and so on. Nonetheless, if the very first HR value is unknown, our invention is able to estimate it from $\tilde{HR}$.

Continual Learning (409)

The continual learning block 409 implements a continual learning approach that uses the own user's data to improve the exponential approximation model by optimizing the eight trainable parameters previously described. The core idea is: if the HR obtained from the PPG-based approach is available and the quality flag is reliable, it is possible to fine-tune the exponential approximation model parameters in real-time. Essentially, this feature works as a model personalization for a given user.

Let us consider y and $\hat{y}$ to be the HR estimated from the PPG-based approach and from exponential approximation model, respectively. In order to achieve a continual learning, we perform the gradient descent algorithm using the derivatives of the mean absolute error (MAE) throughout the time. The MAE is defined by the following equation:

$$MAE(y, \hat{y}) = \frac{1}{N} \sum_{i=0}^{N} |y_i - \hat{y}_i| \quad (5)$$

Since the MAE is not continuous, which is problematic to use the gradient descent strategy, we use the module definition to compute the derivatives for $y_i - \hat{y}_i > 0$ with respect to $\Theta = \{W, \tau, b_{low}, b_{high}\}$:

$$\frac{\partial MAE(y, \hat{y})}{\partial \Theta} = \frac{\partial}{\partial \Theta}\left[\frac{1}{N}\sum_{i=0}^{N}(y_i - \hat{y}_i)\right] \quad (6)$$

$$= \frac{1}{N}\sum_{i=0}^{N}\frac{\partial(y_i - \hat{y}_i)}{\partial \Theta}$$

$$= \frac{1}{N}\sum_{i=0}^{N}\frac{\partial y_i}{\partial \Theta} - \frac{\partial \hat{y}_i}{\partial \Theta} = \boxed{\frac{1}{N}\sum_{i=0}^{N}-\frac{\partial \hat{y}_i}{\partial \Theta}}$$

When $y_i - \hat{y}_i > 0$, the signal of the derivatives just needs to be inverted.

Now, the derivatives of the HR (t+1) are computed:

$$\frac{\partial HR(t+1)}{\partial \Theta} = \frac{\partial \tilde{HR}}{\partial \Theta} - \frac{\partial}{\partial \Theta}\left[(\tilde{HR} - HR(t))e^{-\frac{1}{\tau}}\right] \quad (7)$$

$$= \frac{\partial \tilde{HR}}{\partial \Theta} - \left[\frac{\partial(\tilde{HR} - HR(t))}{\partial \Theta}e^{-\frac{1}{\tau}} + \frac{\partial e^{-\frac{1}{\tau}}}{\partial \Theta}(\tilde{HR} - HR(t))\right]$$

$$= \frac{\partial \tilde{HR}}{\partial \Theta} - \left[\left(\frac{\partial \tilde{HR}}{\partial \Theta} - \frac{\partial HR(t)}{\partial \Theta}\right)e^{-\frac{1}{\tau}} + \frac{\partial e^{-\frac{1}{\tau}}}{\partial \Theta}(\tilde{HR} - HR(t))\right]$$

$$= \boxed{\frac{\partial \tilde{HR}}{\partial \Theta} - \left[\frac{\partial \tilde{HR}}{\partial \Theta}e^{-\frac{1}{\tau}} + \frac{\partial e^{-\frac{1}{\tau}}}{\partial \Theta}(\tilde{HR} - HR(t))\right]}$$

Therefore, for each parameter in $\Theta$, there are the following derivatives:

$$\frac{\partial HR(t+1)}{\partial W} = D_s - D_s e^{-\frac{1}{\tau}} \quad (8)$$

-continued $$\frac{\partial HR(t+1)}{\partial \tau} = -\frac{e^{-\frac{1}{\tau}}}{\tau^2}[D_s \times W^T - HR(t)] \quad (9)$$

$$\frac{\partial HR(t+1)}{\partial \{b_{low}, b_{high}\}} = 1 - e^{-\frac{1}{\tau}} \quad (10)$$

which result in the following parameters update rules:

$$W_{t+1} = W_t - \alpha\left(D_s e^{-\frac{1}{\tau_t}} - D_s\right) \quad (11)$$

$$\{b_{t+1_{low}}, b_{t+1_{high}}\} = \{b_{t_{low}}, b_{t_{high}}\} - \alpha\left(e^{-\frac{1}{\tau_t}} - 1\right) \quad (12)$$

$$\tau_{t+1} = \tau_t - \alpha\frac{-e^{-\frac{1}{\tau_t}}}{\tau_t^2}[D_s \times W_t^T - HR(t)] \quad (13)$$

where, $\alpha$ is the learning rate and the parameters $b_{low}$ and $b_{high}$ are selected according to the intensity of the workout 413.

The update rule equations are applied throughout the time. In other words, whenever the optimization is allowed, it performs one step of the gradient descent algorithm. In this sense, the personalization pipeline does not save any past workout data within the memory device. Instead, it performs the optimization in real-time.

Therefore, with basis on the exponential heart rate estimation 308 obtained from the exponential approximation model 408, the method is capable of outputting a secondary estimation to the user whenever the PPG signal is unreliable. Hence, according to the present method, if the PPG quality flag 305 is reliable, the PPG heart rate estimation 305 is shown to the user. Otherwise, it shows the exponential heart rate estimation 308.

Manager Block

Returning to FIG. 3, the manager block 315 takes as input the HR estimated using the PPG-based method 304, the quality flag 305, the HR predicted by the exponential approximation model 308, and the personalization timer 309. The main goal of the manager block 315 is to ensure a smooth transition between the HR estimated using the PPG-based method 304 and the HR predicted by the exponential approximation model 308 when the quality flag changes from reliable to unreliable. Essentially, the pipeline illustrated in FIG. 4 with the accelerometer preprocess block 415 and the prediction block 416 is enough to predict the HR even without using the PPG signal. Nonetheless, since it is preferably intended to support the estimation provided by the PPG-based method, it turns out that transitioning between the methods when the quality flag changes may lead to strong discontinuity in the HR curve when both estimations disagree with each other. Therefore, the manager block 315 implements an algorithm in order to make the transition smoother and more natural.

There are two transition possibilities: (1) when the quality flag changes from reliable to unreliable and it is necessary to switch the estimation from the PPG-based approach to the exponential approximation model; (2) when the flag quality changes from unreliable to reliable and the PPG-based approach takes back the control over the HR estimation based on the exponential approximation model. In both cases, a stabilization equation is applied with basis on the exponential approximation that was described in the previous sections:

$$\widetilde{HR}(t) = HR_{Target} - (HR_{Target} - \widetilde{HR}(t-1)) \times e^{-\frac{\Delta t}{\sigma}} \quad (14)$$

where:

$\widetilde{HR}(t)$ is the transition HR;

$\widetilde{HR}(t-1)$ is the HR obtained right before the transition starts;

$HR_{Target}$ is the target HR (from PPG-based approach or exponential approximation model) in which $\widetilde{HR}(t)$ must stabilize;

$\Delta t$ is one step of time that depends on the PPG signal frequency; and $\sigma$ controls how fast or slow the transition should happens.

The idea of the transition equation is straightforward: it works as an interpolation function between the transition HR and the target HR. In addition to this equation, the algorithm waits $t_s$ seconds to stabilize the $\widetilde{HR}(t)$, if within this window of time the absolute error between $\widetilde{HR}(t)$ and $HR_{Target}$ is greater than Es bpm, the algorithm forces it to assume the value of $HR_{Target}$.

Figure 5:
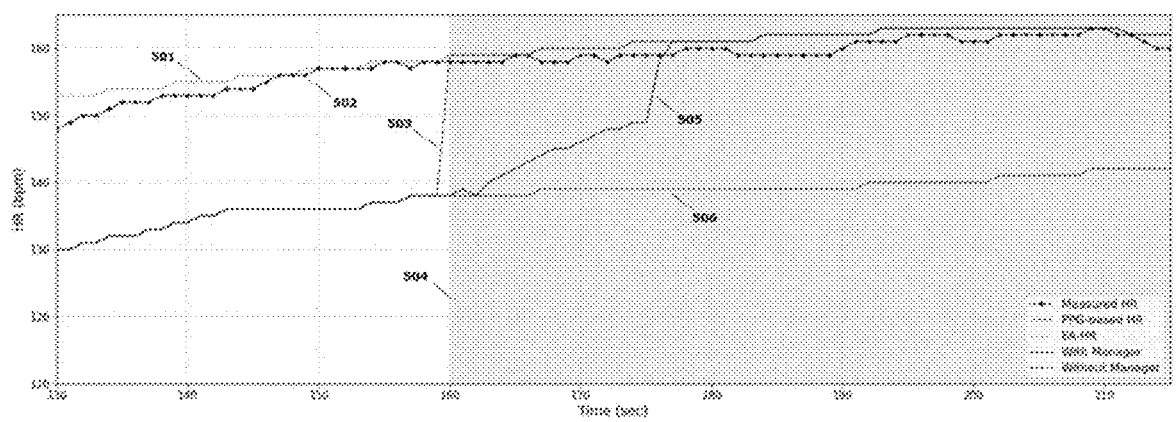
FIG. 5 shows an illustration of the difference between the exponential approximation (EA) model with and without the Manager block, according to an embodiment of the present invention.

In order to illustrate how the manager block 315 works, in FIG. 5 is illustrated an example of the HR estimation for part of a running session using and without using the manager. As it was previously described, the manager block 315 outputs the final HR 310, which is basically the composition of the estimation obtained from the PPG-based approach and the exponential approximation model. As we may see, FIG. 5 presents the measured HR 502, the HR obtained from the PPG signal 506, and the exponential approximation model estimation 501. When the time is 160s the quality flag 305 changes from reliable to unreliable, which is indicated by the grey area 504. Therefore, the manager block 315 must switch from the PPG-based method to the exponential approximation model. However, as we may observe, the estimations 506 and 501 disagree too much with each other. In this case, the PPG-based method is far from the reference 502. Thus, the HR curve indicated by 503 shows the result without applying the transition algorithm, while the HR curve indicated by 505 applies it. As we can note, curve 503 presents a significant discontinuity, since the transition is hard. On the other hand, curve 505 presents a smoother transition, which looks more natural and closer to a HR curve than 503.

It is interesting to note that the transition enforced by the manager block 315 may lead to a higher MAE when compared to the same result without applying it. It is easy to note it by observing that the curve 503 is closer to curve 501 than curve 506. Indeed, it is a trade-off between MAE and integrity of the HR curve. The magnitude of this error is controlled by the transition parameters $\sigma$, $t_s$ and $E_s$. If the integrity is more important in this situation, the manager block 315 must always be applied as described in this section.

Beyond ensuring the smooth transition between the HR estimations, the manager block 315 also decides when to switch the estimations. The simplest approach would be switching them whenever the quality flag 305 changes from reliable to unreliable and vice-versa. However, since the model is personalized throughout the time, in order to increase performance, safeness, and integrity, preferably, a personalization threshold time ($\rho_t$) that the model must achieve before allowing it to take control of the final HR estimation may be defined. In other words, the threshold time ($\rho_t$) indicates the minimum required training time for the EA model before usage. The idea is straightforward, the manager block 315 takes as input the personalization timer 309 and if it is greater than $\rho_t$ the transition is allowed; otherwise, the manager always estimates the HR and quality flag 305 obtained in the PPG-based method according to block 312.

A Step-by-Step Example of the Proposed Invention

In order to thoroughly illustrate the present method's workflow, a step-by-step example will be described to exemplify each block, input, and output presented in FIGS. 3 and 4. The method outputs a new HR estimation every second. However, the length of the accelerometer and PPG input data depends on their frequency. The method works with any frequency, but for this example, we consider it as 25 Hz. Thereby, let us consider the workout illustrated in FIG. 5. Our goal is to compute all input data for t=160 to predict HR(t=161), where the PPG quality flag is unreliable.

Step 0: Determining the Inputs

First of all, it is necessary to define the inputs for the method. In FIG. 3 is shown that the method takes as input the PPG signal 301, 3-axis of an accelerometer signal 302, and the user's demographics 303. In addition, the proposed invention is agnostic to the PPG-based method, i.e., it works to any method that takes the PPG signal and returns a PPG heart rate estimation 304 and the PPG quality flag 305. For this example, the PPG signal has eight channels. Therefore, we define each input as follows:

PPG signal 301: since the signal is in 25 Hz and it has four channels, every second it produces a matrix P with shape equal to 25×8. For t=160 s:

$$P[t=160] = \begin{bmatrix} 2089748 & 2086539 & 2115013 & 2112156 & 2156491 & 2153313 & 2091474 & 2088684 \\ 2089596 & 2086430 & 2114686 & 2111859 & 2155502 & 2152341 & 2088431 & 2085606 \\ 2087929 & 2084675 & 2113062 & 2110150 & 2153447 & 2150199 & 2084467 & 2081603 \\ 2082910 & 2079733 & 2111380 & 2108488 & 2151776 & 2148593 & 2081051 & 2078252 \\ 2074159 & 2071119 & 2109006 & 2106114 & 2149836 & 2146545 & 2075538 & 2072827 \\ 2066701 & 2063673 & 2103027 & 2100164 & 2144712 & 2141419 & 2069958 & 2067335 \\ 2066505 & 2063429 & 2099769 & 2096931 & 2142078 & 2138788 & 2068515 & 2065962 \\ 2068123 & 2064939 & 2098844 & 2096027 & 2141568 & 2138215 & 2067951 & 2065386 \\ 2068589 & 2095552 & 2098277 & 2095490 & 2141424 & 2138134 & 2069159 & 2066770 \\ 2069563 & 2066545 & 2097912 & 2095197 & 2141659 & 2138321 & 2070910 & 2068655 \\ 2070158 & 2067201 & 2097820 & 2095109 & 2141593 & 2138315 & 2071155 & 2068982 \\ 2071418 & 2068540 & 2097811 & 2095165 & 2141488 & 2138272 & 2071331 & 2069210 \\ 2072402 & 2099428 & 2097633 & 2094930 & 2141389 & 2138144 & 2070715 & 2068447 \\ 2065228 & 2062246 & 2095263 & 2092542 & 2140036 & 2136794 & 2068484 & 2066330 \\ 2065804 & 2062656 & 2092229 & 2089390 & 2137009 & 2133727 & 2061535 & 2058897 \\ 2066885 & 2063607 & 2090918 & 2088008 & 2136085 & 2132786 & 2061443 & 2058689 \\ 2068619 & 2065291 & 2089735 & 2086822 & 2134557 & 2131244 & 2060940 & 2058108 \\ 2071091 & 2067797 & 2088670 & 2085726 & 2132321 & 2129009 & 2061019 & 2058121 \\ 2072900 & 2069550 & 2087835 & 2084859 & 2130807 & 2127508 & 2061139 & 2058224 \\ 2076632 & 2073303 & 2086575 & 2083592 & 2128321 & 2125071 & 2060077 & 2057209 \\ 2079849 & 2076510 & 2086206 & 2083238 & 2127044 & 2123745 & 2060131 & 2057165 \\ 2080273 & 2076872 & 2086386 & 2083394 & 2127030 & 2123757 & 2060741 & 2057784 \\ 2080646 & 2077123 & 2086478 & 2083437 & 2126885 & 2123581 & 2061106 & 2058123 \\ 2079845 & 2076516 & 2086165 & 2083179 & 2126823 & 2123532 & 2061210 & 2058254 \\ 2076295 & 2072957 & 2086437 & 2083463 & 2127406 & 2124122 & 2060115 & 2057261 \end{bmatrix}$$

Accelerometer signal 302: since the signal is in 25 Hz and it has 3 axis (x, y, z), every second it produces a matrix A with shape equal to 25×3:

$$A[t=160] = \begin{bmatrix} -2.138785 & -6.275047 & -6.557664 \\ -2.639352 & -2.483673 & -4.92663 \\ -3.791374 & -9.630521 & -4.905075 \\ -0.342493 & -7.187563 & -11.481899 \\ 3.683596 & -11.077135 & -17.024059 \\ 6.689392 & -16.65522 & -17.172552 \\ 8.013858 & -12.293823 & -11.314245 \\ 5.848727 & -7.795908 & -5.352951 \\ 7.45102 & -4.418879 & -3.662041 \\ 7.764772 & -1.872934 & -0.84785 \\ 7.316896 & -0.052691 & -0.584394 \\ 7.889315 & 0.320938 & -0.392789 \\ 7.87255 & -3.441696 & -2.99861 \\ 12.054317 & -17.613243 & -15.821741 \\ 3.932682 & -17.287516 & -11.239999 \\ 4.737421 & -18.726944 & -9.989779 \\ 0.383209 & -14.851744 & -4.579348 \\ -1.350812 & -9.570644 & -1.250219 \\ -2.375896 & -6.804355 & 0.067062 \\ -3.695572 & -1.257404 & 2.35434 \\ -3.240511 & -1.698095 & 0.337703 \\ -3.472831 & -5.98764 & 1.281355 \\ -4.138657 & -10.928641 & -2.986635 \\ -0.589184 & -15.335545 & -6.466652 \\ 0.42153 & -23.186539 & -7.407909 \end{bmatrix}$$

User's demographics 303: in this example, the physical activity is performed by a 23 year old woman, weighting 61.6 kg, and 1.63 m tall. Therefore, the demographics is represented by an array d=[BMI, age, male, female], where BMI=(weight/height$^2$). Thus:

$d=[23.2, 23, 0, 1]$

The PPG data P 301 and the accelerometer data A 302 are the inputs for the block 312, which represents the PPG-based method. As previously mentioned, the model proposed by the present invention is agnostic to this method. Thus, what is important is that we need to get the PPG-based HR estimation 304 and the PPG quality flag 305. For this example, they assume the following values $HR_{ppg}(t=160)$= 149 and $Flag_{PPG}$=unreliable, respectively, the $Flag_{PPG}$ being the quality indicator.

Step 1: Determining the Activity Levels

In this step, the activity levels are obtained, which represents the user's motion information. To do so, the Accelerometer preprocess block 415 is carried out, which is composed of the Filtering and aggregation 405, Activity level computation 406, and intensity handler 407 subblocks.

Following the workflow presented in FIG. 4, firstly, a band-pass Finite Impulse Response (FIR) filter is applied to the accelerometer data A 302 with order and cut-off frequencies equal to 2 and (8 Hz, 12 Hz), respectively. It results in the $A_f$ matrix illustrates as follows:

$$A_f[t=160] = \begin{bmatrix} 0.13074 & 0.111691 & 1.81941 \\ -0.807174 & 0.466119 & -0.302058 \\ 1.1406 & -0.698129 & -0.206817 \\ -0.947085 & -0.0817589 & 0.760386 \\ 1.17441 & 0.312469 & -2.10798 \\ -0.415808 & 0.335904 & 1.74074 \\ -0.259664 & -1.97762 & -0.0698531 \\ 0.108237 & 3.8155 & 0.837646 \\ -0.656075 & -2.61985 & -0.717031 \\ 1.04344 & 1.02823 & -0.24824 \\ -0.708639 & -0.551846 & 0.314202 \\ 0.0838374 & 0.356188 & -0.299165 \\ 0.203105 & -0.600293 & -0.126399 \\ -0.0884237 & -0.130125 & -0.0736323 \\ 0.423789 & -1.46469 & -1.5893 \\ -1.73565 & 2.9545 & 3.45506 \\ 1.67703 & -1.16453 & -1.64657 \\ -0.506416 & 0.0344491 & -0.0128342 \\ -0.670234 & 1.26076 & 0.90922 \\ 1.5553 & -1.85453 & -1.58975 \\ -1.61626 & 1.79429 & 1.50276 \\ 1.52287 & -1.94451 & -1.65235 \\ -1.16706 & 0.448869 & 1.41903 \\ 0.716502 & -0.177439 & -1.43413 \\ 0.071052 & 0.387287 & 0.702242 \end{bmatrix}$$

Next, each row of $A_f$ matrix is aggregated using Equation (1) to obtain the aggregated accelerometer Agg array:

$$Agg[t=160] = \begin{bmatrix} 1.82752 \\ 0.979814 \\ 1.35319 \\ 1.21731 \\ 2.4332 \\ 1.82096 \\ 1.99582 \\ 3.90786 \\ 2.79431 \\ 1.48582 \\ 0.951539 \\ 0.47265 \\ 0.646205 \\ 0.173703 \\ 2.20245 \\ 4.86611 \\ 2.62293 \\ 0.507749 \\ 1.69275 \\ 2.89578 \\ 2.8443 \\ 2.97162 \\ 1.89134 \\ 1.61294 \\ 0.805099 \end{bmatrix}$$

The Agg array is the output 410 of the Filtering and aggregating module 405, which is the input of the Activity level and computation module 406.

The activity level raw $AL_{raw}$ 411 is computed through Equation (2), which results in the following array:

$$AL_{raw}[t=160] = \begin{bmatrix} 2.07478 \\ 2.06757 \\ 2.05906 \\ 2.06280 \\ 2.06039 \\ 2.05974 \\ 2.07822 \\ 2.08538 \\ 2.07939 \\ 2.06811 \\ 2.05215 \\ 2.03809 \\ 2.01945 \\ 2.02128 \\ 2.04973 \\ 2.05546 \\ 2.03998 \\ 2.03651 \\ 2.04510 \\ 2.05310 \\ 2.06228 \\ 2.06057 \\ 2.05610 \\ 2.04359 \\ 2.03353 \end{bmatrix}$$

The activity level AL 412 is also computed through Equation (2), but using the normalized version of the $A_{gg}$ array, which results in the following:

$$AL[t=160] = \begin{bmatrix} 0.910841 \\ 0.911733 \\ 0.912615 \\ 0.913489 \\ 0.914354 \\ 0.915211 \\ 0.916059 \\ 0.916898 \\ 0.917729 \\ 0.918067 \\ 0.913613 \\ 0.910939 \\ 0.903566 \\ 0.904531 \\ 0.905486 \\ 0.906431 \\ 0.902444 \\ 0.903419 \\ 0.904385 \\ 0.905341 \\ 0.906288 \\ 0.907225 \\ 0.908153 \\ 0.907122 \\ 0.908051 \end{bmatrix}$$

This array represents the activity level AL 412, which is the output of the Accelerometer preprocess block 415. Finally, the intensity of the workout IW 413 is determined within the Intensity handler module 407. For this example, we set the threshold $\varphi_t=1.25$ and $t_\varphi=5$, which results the state high. It is worth to note that the algorithms to compute such measurements are not essential to this invention. Although they are important to the next block and module, they refer to preferential features of the invention.

Step 2: Predicting the HR and Updating the Trainable Parameters

As previously stated, the Prediction block 416 is a key component of our invention. It takes as input the AL= [t=160] array 412, IW[t=160] 413, demographics, d, 303, and for this example, the previous HR(t) 403 is represented by $HR_{PPG}=(t=160)$ (since the goal is to predict HR(t=161), the previously HR available is the one obtained by the PPG. If we want to predict HR(t=162), for example, the previous HR would be HR(t=161) since the PPG signal will be unreliable).

The predicted HR is computed according to Equations (3) and (4). To do so, we need to define the parameters W, $\tau$, $b_{low}$ and $b_{high}$. For this example, they are defined as follows:

$$W=\{80, 0.82, -0.9, -6.44, -0.09\}$$

$$b_{low}=80, b_{high}=120, \text{ and } \tau=75$$

Next, from Equation (4), we obtain $\widetilde{HR}=139.16$. Next, from Equation (3), we obtain the HR estimated from the EA model 408 for $HR_{EA}-(t=161)=140$ which represents the output 308.

After estimating the HR, the next step is to perform the Continual Learning (personalization) module 409. This module takes the EA model parameters (W, $\tau$, $b_{low}$ and $b_{high}$), the $HR_{EA}$, $HR_{PPG}$, and $Flag_{PPG}$ to perform the personalization algorithm whenever the $Flag_{PPG}$=reliable. Thus, for this example, the personalization is not performed since the $Flag_{PPG}$=unreliable. However, let us suppose that in t=180 the $Flag_{PPG}$ becomes reliable. In this case, to update (W, $\tau$, $b_{low}$ and $b_{high}$) it is necessary to perform Equations (11), (12), and (13) with a=5.0, which fine-tunes the EA Model according to the error between the $HR_{EA}-$(t=180) and $HR_{PPG}=$(t=180). In addition, the personalization module returns the personalization timer 309, which represents the amount of time in seconds that the EA Model was fine-tuned to the current user.

In this step, there are two features that further differentiate this invention from the prior art methods. First, we propose a new dynamic and recursive exponential function (Equation (4)) that is able to adapt to different user's demographics and workout intensity. Second, the personalization runs in real-time, without saving or using any user data in the device's memory. Due to memory limitations in wearable devices, this represents a great advantage when compared to the prior art.

Step 3: Delivering the Final HR Prediction

As previously mentioned, the proposed invention ensures that the EA Model and the PPG-based method work in a collaborative way. To do so, the last step is to perform the transition algorithm within Manager block 315, which is important to ensure the smoothness and integrity of the HR final curve (see FIG. 5). Whenever the $Flag_{PPG}$ changes from unreliable to reliable (or vice-versa), Equation (14) is applied to achieve the final HR prediction 310. If there is no change, the transition is not applied. Therefore, for this example, we perform Equation (14) using the following parameters: $'\phi=5$, $\rho_t=120$, $\Delta t=1/25$, $\sigma=25$, $t_s=10$, and $E_s=3$.

This results in $\widetilde{HR}(t=161)=139$, which is the output 310. The final quality flag 311 depends on the personalization threshold time ($\rho_t$) and the $Flag_{PPG}$. If $Flag_{PPG}$=reliable, the final quality flag is always reliable. On the other hand, if $Flag_{PPG}$=unreliable and the personalization timer 309 is greater than $\rho_t$, the final quality flag is reliable. Otherwise, unreliable. For this example, we set $\rho_t=120$, which means that the EA Model must be personalized for the user for 120 seconds to be able to collaborate with the PPG-based method. To predict $\tilde{HR}$ (t=162), all steps must be performed again.

This step is another difference from the prior art methods. In brief, the transition algorithm (Equation (14)) is important to avoid strong discontinuities in the HR final curve (see FIG. 5), which makes it unnatural and unreliable. In addition, it ensures a better prediction of the regression model since we force the model's personalization for $\rho_t$ seconds.

Alternative Embodiments

As described in the previous section, the best mode of the present invention is to support the HR estimation of a PPG-based method. Nonetheless, beyond this application, this invention may be adapted to work for other problems that we describe in the following.

Predicting the HR Curve Using Few Data

Figure 6:
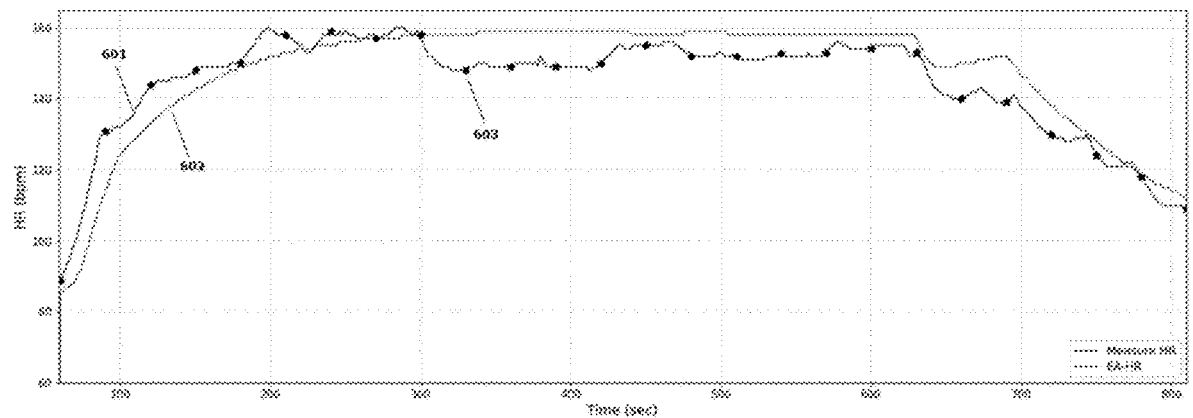
FIG. 6 shows an example of the EA model estimating the HR curve for the whole workout using a few data points from the original signal, according to an embodiment of the present invention.

It is possible to use the EA model to predict the HR curve for a given workout session using only a few data points sampled from the original activity level (AL) measurements. This scenario is illustrated in FIG. 6 where the measured HR curve 601 is sampled into multiple time points indicated by 603. For each time point, we save the AL that is computed during the real-time estimation. From these values, we approximate the HR curve 602 using the EA model. This application may be interesting to predict the whole HR curve of a past workout by saving just a few data points related to it.

Saving Battery Life

Figure 7:
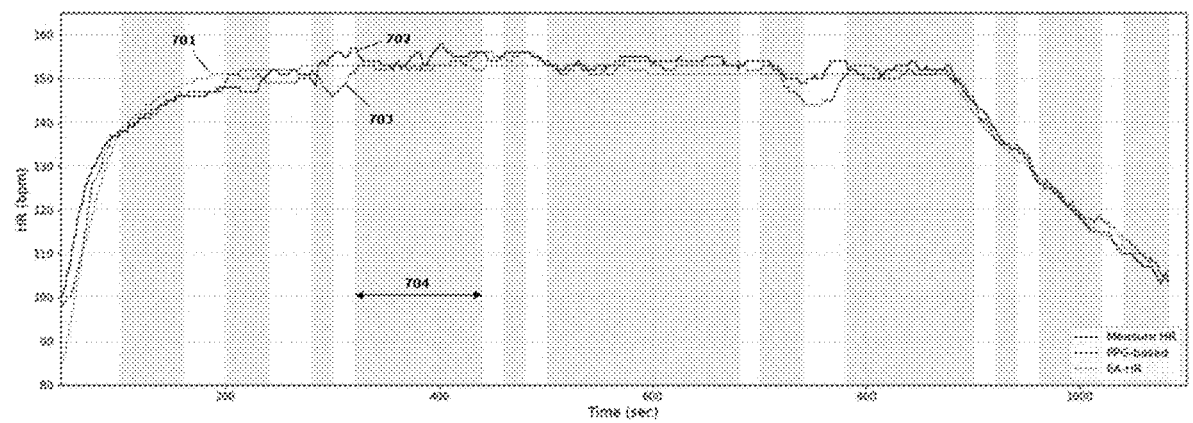
FIG. 7 shows an example of the saving battery scenario in which the HR estimation is intercalated between the PPG and Accelerometer based methods, according to an embodiment of the present invention.

Although PPG-based methods provide reliable HR estimation, the PPG sensor consumes much more energy than the accelerometer. The PPG may take up to 5000 times more energy than the accelerometer. Obviously, it directly affects the device's battery lifetime and hinder its autonomy. In this sense, the present invention may be adapted to assist the host device to save battery by intercalating the HR estimations from the PPG and the accelerometer signals according to a given rule. In FIG. 7 is illustrated a use case scenario that exemplify how the EA model may be adapted to save the device's battery. In this figure is presented the HR estimated from the PPG 702 and the accelerometer 701 signals. As we may see, they are both close to the reference HR represented 702. The grey areas 704 show when the estimation from the accelerometer should be replaced by the PPG one. In this case, we define the following rule: in every ns seconds, we compare the performance of the HR obtained from the PPG-based and the EA model. If the difference between them is lower than E bpm, the device would stop the PPG measurements for the next ns seconds and the result HR estimation would come from the EA model. On the other hand, if the different is greater than E bpm, the estimation would keep coming from the PPG-based method until the difference be measured again (within ns seconds) and start the cycle again. In this example, the accelerometer is applied to estimate the HR in 68.5% of the time. Since it spends less battery than the PPG, this approach would save the devices battery.

Hardware Implementation

The example embodiments described herein may be implemented using hardware, software or any combination thereof and may be implemented in one or more computer systems or other processing systems. Additionally, one or more of the steps described in the example embodiments herein may be implemented, at least in part, by machines. Examples of machines that may be useful for performing the operations of the example embodiments herein include wearable electronic devices, such as smartwatches.

For instance, one illustrative example system for performing the operations of the embodiments herein may include one or more components, such as one or more microprocessors, for performing the arithmetic and/or logical operations required for program execution, and storage media, such as one or more disk drives or memory cards (e.g., flash memory) for program and data storage, and a random access memory, for temporary data and program instruction storage.

Therefore, the present invention is also related to a wearable electronic system for predicting the heart rate (HR) of a user during a physical activity comprising a processor, and a memory comprising computer readable instructions that, when performed by the processor, causes the processor to perform the method steps previously described in this disclosure.

The system may also include software resident on a storage media (e.g., a disk drive or memory card), which, when executed, directs the microprocessor(s) in performing transmission and reception functions. The software may run on an operating system stored on the storage media, such as, for example, UNIX or Windows, Linux, Android, and the like, and can adhere to various protocols such as the Ethernet, ATM, TCP/IP protocols and/or other connection or connectionless protocols.

As is well known in the art, microprocessors can run different operating systems, and can contain different types of software, each type being devoted to a different function, such as handling and managing data/information from a particular source, or transforming data/information from one format into another format. The embodiments described herein are not to be construed as being limited for use with any particular type of server computer, and that any other suitable type of device for facilitating the exchange and storage of information may be employed instead.

Software embodiments of the illustrative example embodiments presented herein may be provided as a computer program product, or software, that may include an article of manufacture on a machine-accessible or non-transitory computer-readable medium (also referred to as "machine-readable medium") having instructions. The instructions on the machine accessible or machine readable medium may be used to program a computer system or other electronic device. The machine-readable medium may include, but is not limited to, floppy diskettes, optical disks, CD-ROMs, and magneto-optical disks or other type of media/machine readable medium suitable for storing or transmitting electronic instructions.

Therefore, the present invention also relates to a non-transitory computer readable storage medium for predicting the heart rate (HR) of a user during a physical activity, comprising computer readable instructions that, when performed by the processor, causes the processor to perform the method steps previously described in this disclosure.

The techniques described herein are not limited to any particular software configuration. They may be applicable in any computing or processing environment. The terms "machine-accessible medium", "machine-readable medium" and "computer-readable medium" used herein shall include any non-transitory medium that is capable of storing, encoding, or transmitting a sequence of instructions for execution by the machine (e.g., a CPU or other type of processing device) and that cause the machine to perform any one of the methods described herein. Furthermore, it is common in the art to speak of software, in one form or another (e.g., program, procedure, process, application, module, unit, logic, and so on) as taking an action or causing a result. Such expressions are merely a shorthand way of stating that the execution of the software by a processing system causes the processor to perform an action to produce a result.

Effect

In order to evaluate the effect of the method according to the present invention, experiments were carried out using three different exercise datasets performed on treadmills that were collected:

Walking: a dataset containing 103 different subjects performing a three different walking sessions from 10 to 15 minutes totaling 4,625 minutes of data.

Running: a dataset containing 136 different subjects performing a three different running sessions from 12 to 18 minutes totaling 5,464 minutes of data.

Walk-and-run: a dataset containing 14 different subjects that intercalates in the same session one minute walking and two minutes running until reach 10 minutes. There are six different sessions totaling 881 minutes of data.

In each dataset, all subjects wear a Polar H10 chest strap to measure the reference HR using ECG and a Galaxy Watch 3 device to collect the PPG and accelerometer signals.

To play the role of the PPG-based approach, the latest HR estimation algorithm from Samsung Galaxy Watch 3 (GW3-HR), which uses multiple PPG channels and the 3-axis of the accelerometer to output the HR, was used. In addition, this algorithm returns a flag that classifies the PPG signal as reliable or unreliable (most of the time, the flag becomes unreliable because of MA). As a baseline method for comparison, a Multilayer Perceptron (MLP) was applied with 2 hidden layers containing 6 neurons each. This may be seen as an adaptation of the method proposed by McCoville et. al [3] that allows the use of an online personalization similar to the one described in the first embodiment. For all experiments, the methods' performances are evaluated according to the following metrics:

The mean average error (MAE) in beats per minute (bpm). The lower the better.

The workout coverage (COV) that is the % of time in which the quality flag is reliable. In other words, it shows the % of time the user sees a HR prediction on the device's display. The higher the better.

method for each dataset considering the entire workout. In other words, the results consider both the reliable and unreliable quality flags and the PPG-based approach GW3-HR and the EA model are working individually, i.e., the manager block is not applied. As we may see, the GW3-HR estimation is generally better than the other methods, which is expected since it uses the PPG signal as primary source. Nonetheless, the EA model outputs a fair HR estimation, in particular for the walking dataset. In addition, its performance is better than the MLP for all dataset and metrics.

TABLE 1 the performance of each method for each dataset considering the entire workouts

| Dataset | GW3-HR | | EA model | | MLP | |
| --- | --- | --- | --- | --- | --- | --- |
| | MAE (bpm) | PR (%) | MAE (bpm) | PR (%) | MAE (bpm) | PR (%) |
| Walking | 5.58 ± 6.13 | 70.33 ± 33.95 | 6.06 ± 5.67 | 78.9 ± 27.75 | 10.98 ± 6.62 | 51.82 ± 34.67 |
| Running | 6.37 ± 6.19 | 69.36 ± 27.43 | 8.16 ± 4.89 | 66.13 ± 26.47 | 12.41 ± 7.61 | 51.56 ± 27.59 |
| Walk-and-run | 3.66 ± 2.71 | 87.87 ± 14.43 | 5.32 ± 2.77 | 85.11 ± 16.29 | 12.28 ± 3.07 | 53.73 ± 12.64 |

In Table 2 is shown the performance of the GW3-HR method stratified by quality flag. As we may note, the method's performance when the quality flag is unreliable is much worse than considering only the reliable one. As previously described, most of the time the unreliable flag occurs due to MA. In this way, our goal is to improve the GW3-HR performance presented in Table 1 by replacing the unreliable HR estimations by the ones obtained using our invention. For example, considering the walking dataset, our method would run around 13% of the time to cover the unreliable flag. The GW3-HR covers the rest of the time. Therefore, both methods work in a collaborative way, which is ensured by the manager block.

TABLE 1 the performance of the GW3-HR stratified by quality flag. The coverage considering both quality flags together does not sum to 100% because the algorithm may take a few seconds to start the estimation.

| Dataset | All | | | Reliable | | | Unreliable | | |
| --- | --- | --- | --- | --- | --- | --- | --- | --- | --- |
| | MAE (bpm) | COV (%) | PR (%) | MAE (bpm) | COV (%) | PR (%) | MAE (bpm) | COV (%) | PR (%) |
| Walking | 5.58 ± 6.13 | 86.74 ± 28.62 | 70.33 ± 33.95 | 4.56 ± 4.54 | 75.77 ± 34.82 | 85.42 ± 21.51 | 15.04 ± 9.63 | 10.98 ± 23.55 | 32.47 ± 36.71 |
| Running | 6.37 ± 6.19 | 90.1 ± 21.85 | 69.36 ± 27.43 | 4.37 ± 3.0 | 66.6 ± 35.08 | 85.88 ± 17.66 | 14.04 ± 9.12 | 23.5 ± 31.95 | 39.55 ± 34.48 |
| Walk-and-run | 3.66 ± 2.71 | 96.28 ± 6.7 | 87.87 ± 14.43 | 3.02 ± 1.51 | 84.81 ± 22.3 | 94.72 ± 7.37 | 9.2 ± 6.56 | 11.47 ± 21.23 | 62.82 ± 35.25 |

The pass rate (PR) that is the % of time in which the MAE is lower than 10 bpm. The higher the better.

First of all, the accuracy of the HR prediction the EA model was assessed by comparison with the other ones. In Table 1 is presented the performance of each HR estimation In Table 3 is presented the performance of both EA model+Manager (PEM) and MLP+Manager replacing the HR estimation when the quality flag of the GW3-HR is unreliable. For both methods, the manager block 315 performs the HR transition when the quality flag changes in the same way as described in the first embodiment. First of all, comparing the results of the Manager-like methods with the GW3-HR in Table 2, we note that the performance, in terms of MAE and PR, improved for the stratification all and is close to the reliable one. As expected, replacing the unreliable method by the manager results in a better performance if compared to using only the GW3-HR alone. It is interesting to note that the GW3-HR also applies a traditional algorithm to deal with MA; however, it is not enough to produce a proper estimation during the whole workout. Lastly, the coverage for both stratifications is slightly lower because of the integrity rule defined by the personalization threshold time ($p_r$), which is set to 120 seconds.

TABLE 2 the performance of the PEM and MLP working in collaboration with the GW3-HR, which is run by the manager block

| Dataset | PEM | | | MLP + Manager | | |
|---|---|---|---|---|---|---|
| | MAE (bpm) | COV (%) | PR (%) | MAE (bpm) | COV (%) | PR (%) |
| Walking | 4.2 ± 3.01 | 79.91 ± 33.23 | 86.7 ± 18.69 | 5.01 ± 4.04 | 79.8 ± 31.78 | 81.63 ± 24.86 |
| Running | 4.63 ± 3.11 | 71.25 ± 34.28 | 83.95 ± 19.23 | 5.76 ± 5.63 | 76.12 ± 33.25 | 80.1 ± 23.66 |
| Walk-and-run | 3.26 ± 1.69 | 95.12 ± 8.65 | 93.61 ± 9.48 | 4.0 ± 2.52 | 95.7 ± 8.09 | 90.28 ± 12.86 |

Comparing the performance of the Manager using the EA model (PEM) and the MLP, we see that the average performance for our invention is better than the MLP for all datasets. In addition to better performance, there are other two advantages of using the PEM rather the MLP:

It demands much less memory to run the estimation and personalization than the MLP. Since it must work in real-time in devices with strong memory restriction, this characteristic is mandatory.

Since the PEM has only eight trainable parameter it is easier to personalize for a given user, to explain the contribution of each parameter (consequently, to debug), and its performance is steady regardless the workout session.

Figure 8:
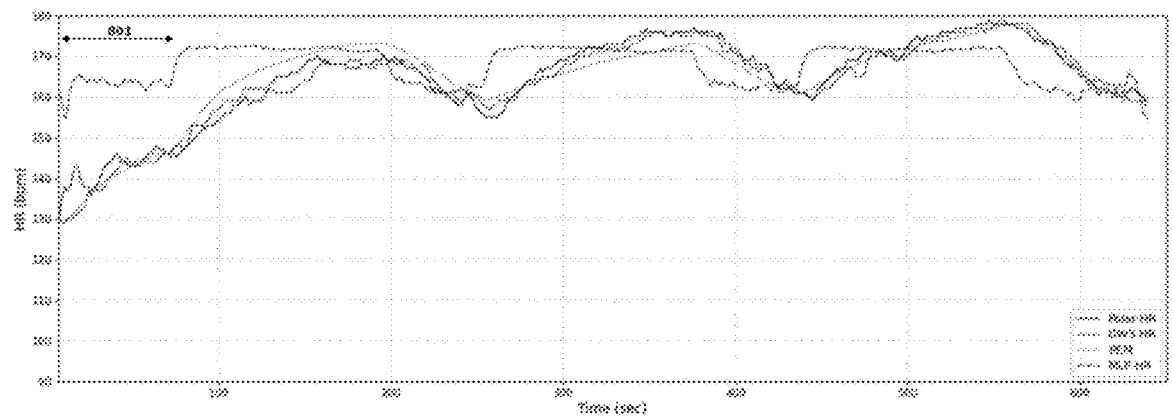
FIG. 8 shows the performance of each method individually for a given workout of the walk-and-run dataset, according to an embodiment of the present invention.

In FIG. 8 is depicted an example of the performance of each method individually for a given workout session of the walk-and-run dataset. In this workout, the performance of the GW3-HR and the PEM in terms of MAE is quite close, 1.64 and 2.78 bpm, respectively. On the other hand, the MLP performance is 7.84, which far from the other methods. In addition, 801 indicates a region in which the MLP presents a quite wrong estimation. This behavior is common for this method and it is hard to identify the reason since we do not know the role of each parameter in this model. The HR curve obtained by the PEM looks more natural and results in better performance than the MLP one.

Figure 9:
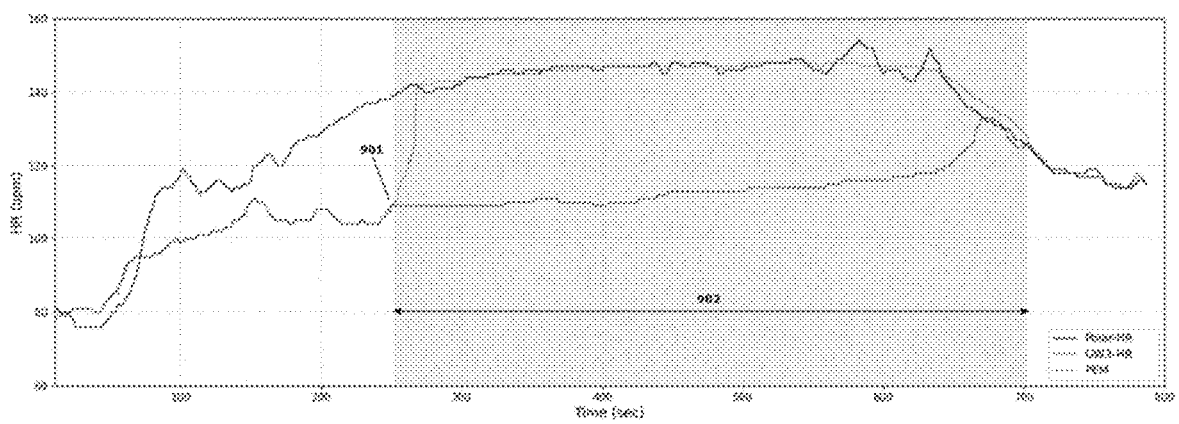
FIG. 9 shows the performance of the GW3-HR with the support of the present invention for a given workout for the running dataset, according to an embodiment of the present invention.

Finally, in FIG. 9 is illustrated an example of the collaboration between the EA model and the GW3-HR provided by the manager block, which is the PEM. As we can see, 901 indicates the start of the transition between the methods, i.e., when the quality flag switches from reliable to unreliable. In this workout, the unreliable flag remains as unreliable for the entire grey area 902. It is easy to see the improvement that the manager introduces into the algorithm. Quantitatively, in terms of MAE, it decreases from 22.2 to 3.31 bpm, which demonstrates the benefits of the present invention.

Technical Advantages of the Proposed Solution

In view of the foregoing, the present invention provides a solution based on the collaboration of the comparison between the HR estimation from motion information and a PPG based method to improve the final estimation. In addition, the present invention proposes the use of only one regression model designed from an exponential function, which allows to output the HR estimation without using multiple models. Further, the present invention relies only in the current user data without using previous data or data from a plurality of users to achieve personalization. Finally, the present invention proposes alternative embodiments wherein a transition equation is applied to improve the smoothness and integrity of the final HR estimated from the collaboration between the proposed exponential model and the PPG-based approach.

The present invention proposes an exponential approximation model developed to estimate the HR of a given person. Using an exponential function over time to model cardiovascular kinetics was previously presented by Hill & Lupton [1] and Zakynthinaki [2]. Although the assumption that the HR may be approximated by an exponential function is correct, proposing such a function and parametrize it is challenging because the HR profile of a well-trained and a sedentary person is quite different and the previously models do not consider it. In addition, they do not present an approach to dynamically consider both the increase and decrease of the HR curve. In this way, the non-obviousness characteristics that differs the exponential regression model of the present invention from the others are described as follow:

it dynamically updates the HR estimated in real-time based on a motion measurement. In other words, the model does not rely in a constant measurement and for each time t it outputs a new estimation.

its equation incorporates a mechanism to automatically identify when the HR should increase or decrease according to the exponential function.

it also incorporates the user's demographics (age, height, weight, and gender) into its equation in order to adapt the model to different HR profiles.

In addition to the characteristics related to exponential model, the present invention also presents the following innovations:

It has a methodology to personalize the exponential model in real-time without saving any data from the previous workout in the device's memory. In this way, the model is continuously learning the user's HR profile during workout execution in order to improve its estimations.

It presents a transition algorithm to improve the smoothness and integrity of the final HR estimated from the collaboration between the exponential model and the PPG-based approach.

While various example embodiments have been described above, it should be understood that they have been presented by way of example, and not limitation. It will be apparent to persons skilled in the relevant art(s) that various changes in form and detail can be made therein.

What is claimed is:

1. A method for predicting heart rate (HR) of a user during a physical activity using a wearable electronic device, the method comprising:

monitoring the user during the physical activity with the wearable electronic device, the wearable electronic device including a photoplethysmography (PPG) sensor to detect changes in blood volume of the user during the physical activity, an accelerometer to capture acceleration of the user during the physical activity, a memory to store demographic data of the user, data from the PPG sensor and data from the accelerometer and a processor to process the data obtained from the PPG sensor and the data from the accelerometer;

computing, using the data from the PPG sensor and the data from the accelerometer, a PPG heart rate estimate and a PPG quality flag;

computing an exponential heart rate estimate by applying the PPG heart rate estimate, the PPG quality flag and the demographic data of the user in an exponential approximation model;

the exponential approximation model being determined by:

$$HR(t+1) = \widetilde{HR} - [\widetilde{HR} - HR(t)] \times e^{-\frac{1}{\tau}}$$

where, HR (t+1) is the exponential estimate of heart rate, $\widetilde{HR}$ is a parameter that indicates an increase or decrease in that heart rate calculated in a previous iteration, and T is a constant that determines the increase or decrease in rate, where, $\widetilde{HR}$ is determined by:

$$\widetilde{HR} = D_s \times W^T + \{b_{low}, b_{high}\}$$

where $D_s$ is a matrix that defines [AL, BMI, age, male, female], AL is a normalized raw activity level, BMI is a body mass index and male or female assumes 1 or 0, the parameter determined according to intensity of the physical activity of the user and $W^T$ is transposition of a matrix of weights that affect behavior of the exponential approximation model;

outputting, provided the PPG quality flag indicates that the data captured from the PPG sensor is reliable, the PPG heart rate estimate; and outputting, provided the PPG quality flag indicates that the data captured from the PPG sensor is unreliable, the exponential heart rate estimate.

2. The method according to claim 1, further comprising: determining a level of movement and an intensity of the physical activity of the user using the data from the accelerometer.

3. The method according to claim 2, wherein the determining the level of movement and the intensity of the physical activity of the user using the data from the accelerometer comprises:

filtering the data from the accelerometer to reduce noise and aggregating an accelerometer signal using a norm function to produce an aggregated accelerometer value, computing a raw value of activity level, $AL_{raw}$, by integrating the aggregated accelerometer value, computing a normalized raw activity level, AL, and computing the intensity of the physical activity of the raw value of activity level upon a comparison with a defined threshold.

4. The method according to claim 3, wherein the accelerometer signal is aggregated with a norm function defined by:

$$agg(\alpha_x, \alpha_y, \alpha_z) = \alpha_x^2 + \sqrt{\alpha_y^2 + \alpha_z^2}$$

where $a_x$, $a_y$ and $a_z$ represent the 3-axis coordinates of the accelerometer.

5. The method according to claim 4, further comprising: integrating the aggregated signal with a sliding window of time to obtain a raw value of the activity level ALraw; and approximating the aggregated signal with a trapezoidal rule:

$$AL_{raw} = \int_{t_1}^{t_2} agg(a) \approx \Delta a \sum_{k=1}^{N-1} agg(a_k) + \frac{agg(a_n) + agg(a_0)}{2}$$

where a=[$a_x$, $a_y$, $a_z$] and N is a number of data points within the sliding window of time, which depends on a sampling frequency of the accelerometer signal.

6. The method according to claim 5, further comprising: applying a clipping operation to ensure that the raw value of activity level is within [0, 1], integrating the raw value of activity level, and normalizing the integrated raw value of activity level by dividing the integrated raw value of activity level by a size of the sliding window of time.

7. The method according to claim 3, wherein the raw value of activity level assumes a low and a high state, which is determined by a threshold $\varphi_i$, and provided $AL_{raw} < \varphi_i$ for a predefined period of time, the raw value of activity level assumes a low state; otherwise, the raw value of activity level assumes a high state.

8. The method according to claim 1, wherein provided the PPG quality flag is reliable, the exponential approximation model parameters are fine-tuned in real-time as a personalization model for the user.

9. The method according to claim 8, further comprising: performing a gradient descent algorithm using derivatives of a mean absolute error (MAE) throughout time, wherein the MAE is defined by:

$$MAE(y, \hat{y}) = \frac{1}{N} \sum_{i=0}^{N} |y_i - \hat{y}_i|$$

wherein y is the PPG heart rate estimate, $\hat{y}$ is the exponential heart rate estimate.

10. The method according to claim 9, wherein a gradient descent strategy is used with a module definition to compute the derivatives for $y_i - \hat{y}_i > 0$ with respect to $\Theta = \{W, \tau, b_{low}, b_{high}\}$:

$$\frac{\partial MAE(y, \hat{y})}{\partial \Theta} = \frac{\partial}{\partial \Theta} \left[ \frac{1}{N} \sum_{i=0}^{N} (y_i - \hat{y}_i) \right]$$

$$= \frac{1}{N} \sum_{i=0}^{N} \frac{\partial (y_i - \hat{y}_i)}{\partial \Theta}$$

$$= \frac{1}{N} \sum_{i=0}^{N} \frac{\partial y_i}{\partial \Theta} - \frac{\partial \hat{y}_i}{\partial \Theta}$$

$$= \boxed{\frac{1}{N} \sum_{i=0}^{N} -\frac{\partial \hat{y}_i}{\partial \Theta}};$$

when $y_i - \hat{y}_i > 0$, signals of the derivatives are inverted; and the derivatives of HR (t+1) are given by:

$$\frac{\partial HR(t+1)}{\partial \Theta} = \frac{\partial \widetilde{HR}}{\partial \Theta} - \frac{\partial}{\partial \Theta} \left[ (\widetilde{HR} - HR(t)) e^{-\frac{1}{\tau}} \right]$$

-continued $$= \frac{\partial \widetilde{HR}}{\partial \Theta} - \left[\frac{\partial(\widetilde{HR} - HR(t))}{\partial \Theta}e^{-\frac{1}{\tau}} + \frac{\partial e^{-\frac{1}{\tau}}}{\partial \Theta}(\widetilde{HR} - HR(t))\right]$$

$$= \frac{\partial \widetilde{HR}}{\partial \Theta} - \left[\left(\frac{\partial \widetilde{HR}}{\partial \Theta} - \frac{\partial HR(t)}{\partial \Theta}\right)e^{-\frac{1}{\tau}} + \frac{\partial e^{-\frac{1}{\tau}}}{\partial \Theta}(\widetilde{HR} - HR(t))\right]$$

$$= \boxed{\frac{\partial \widetilde{HR}}{\partial \Theta} - \left[\frac{\partial \widetilde{HR}}{\partial \Theta}e^{-\frac{1}{\tau}} + \frac{\partial e^{-\frac{1}{\tau}}}{\partial \Theta}(\widetilde{HR} - HR(t))\right]}.$$

11. The method according to claim 10, wherein the exponential approximation model comprises parameters update rules:

$$W_{t+1} = W_t - \alpha\left(D_s e^{-\frac{1}{\tau_t}} - D_s\right)$$

$$\{b_{t+1_{low}}, b_{t+1_{high}}\} = \{b_{t_{low}}, b_{t_{high}}\} - \alpha\left(e^{-\frac{1}{\tau_t}} - 1\right)$$

$$\tau_{t+1} = \tau_t - \alpha \frac{-e^{-\frac{1}{\tau_t}}}{\tau_t^2}[D_s \times W_t^\top - HR(t)]$$

wherein $\alpha$ is a learning rate of the exponential approximation model.

12. The method according to claim 1, further comprising:
managing a transition between the PPG heart rate estimate and the exponential heart rate estimate when the PPG quality flag changes from reliable to unreliable, or vice-versa.

13. The method according to claim 12, wherein the managing of the transition comprises applying a stabilization equation given by:

$$\widetilde{HR}(t) = HR_{Target} - (HR_{Target} - \widetilde{HR}(t-1)) \times e^{-\frac{\Delta t}{\sigma}}$$

wherein $\widetilde{HR}$ (t) is the transition HR; $\widetilde{HR}$ (t−1) is the heart rate obtained right before the transition starts, $HR_{Target}$ is a target heart rate in which $\widetilde{HR}$ (t) must stabilize; $\Delta t$ is one step of time that depends on the PPG signal frequency; and $\sigma$ controls how fast or slow the transition should happens.

14. The method according to claim 1, further comprising:
counting a personalization timer indicating a period which indicates for how long the exponential approximation model was personalized using data of the user,
comparing the personalization timer with a threshold time, $\tau t$, indicating a minimum required training time, and
provided the personalization timer is lower than the threshold time, outputting the PPG heart rate estimate.

15. The method according to claim 1, wherein a new heart rate estimate is estimated every second.

16. A wearable electronic system for predicting heart rate (HR) of a user during a physical activity, comprising
a processor;
a memory comprising computer readable instructions that, when executed by the processor, causes the processor to perform the method of claim 1.

17. A non-transitory computer readable storage medium which stores computer readable instructions that, when executed by a processor, causes the processor to perform the method of claim 1.

* * * * *

UNITED STATES PATENT AND TRADEMARK OFFICE
CERTIFICATE OF CORRECTION

Page 1 of 1

PATENT NO. : 12,226,196 B2
APPLICATION NO. : 17/679815
DATED : February 18, 2025
INVENTOR(S) : Andre Georghton Cardoso Pacheco et al.

It is certified that error appears in the above-identified patent and that said Letters Patent is hereby corrected as shown below:

In the Claims

Column 25, Line 21:
In Claim 1, delete "T" and insert -- $\tau$ --.

Column 25, Line 66:
In Claim 5, delete "ALraw;" and insert -- $AL_{raw}$; --.

Column 28, Line 20:
In Claim 14, delete "τt," and insert -- $\rho_t$, --.

Signed and Sealed this
Twelfth Day of August, 2025

Coke Morgan Stewart
*Acting Director of the United States Patent and Trademark Office*